United States Patent [19]

Miller et al.

[11] Patent Number: 5,416,029
[45] Date of Patent: May 16, 1995

[54] SYSTEM FOR IDENTIFYING TISSUE SAMPLES

[75] Inventors: Beverly W. Miller, Tarentum; William J. Hayes, Edgeworth, both of Pa.

[73] Assignee: Shandon Inc., Pittsburgh, Pa.

[21] Appl. No.: 127,193

[22] Filed: Sep. 27, 1993

[51] Int. Cl.$^6$ ............... G01N 1/36; G01N 33/48; A01N 1/02

[52] U.S. Cl. ................. 436/176; 422/61; 427/4; 435/1; 435/810; 435/40.52; 436/17; 436/174

[58] Field of Search ............ 435/1, 810; 422/61; 436/63, 174, 176, 17, 18; 252/380; 427/4, 416; 424/3

[56] References Cited

U.S. PATENT DOCUMENTS

| | | | |
|---|---|---|---|
| 4,056,359 | 11/1977 | Janin | 435/301 |
| 4,387,990 | 6/1983 | Yazawa et al. | 422/58 X |
| 5,002,377 | 3/1991 | Battifora et al. | 436/174 X |
| 5,017,376 | 5/1991 | Friemel et al. | 424/409 |
| 5,137,793 | 8/1992 | Cockrell | 428/688 |
| 5,141,741 | 8/1992 | Ishida et al. | 424/59 |
| 5,206,143 | 4/1993 | Horan et al. | 435/810 X |
| 5,214,066 | 5/1993 | Szabo | 514/423 |
| 5,255,585 | 10/1993 | Gordon | 83/100 |
| 5,262,332 | 11/1993 | Selkoe | 436/547 X |
| 5,290,706 | 3/1994 | Camiener | 436/174 |

Primary Examiner—Robert J. Warden
Assistant Examiner—Robert Carpenter
Attorney, Agent, or Firm—Kirkpatrick & Lockhart

[57] ABSTRACT

A system for identifying and tracking samples of biological material during the preparation of that tissue for microscopic evaluation. The system includes a plurality of colored aqueous embedding media, microscope slides marked to correspond to the colored embedding media, and, optionally, color-coded containers for the embedding media. A process for preparing samples of biological material using the identification system is also provided, as well as compositions for several embedding media including one or more coloring agents.

25 Claims, No Drawings

SYSTEM FOR IDENTIFYING TISSUE SAMPLES

BACKGROUND OF THE INVENTION

1. Field of the Invention

The present invention relates to a system and a method for identifying and tracking samples of biological material during the preparation of samples of the material for microscopic inspection. The present invention more particularly relates to a system and a method which uses color-coding to identify and track animal or plant tissue samples during the preparation of samples of that tissue for microscopic inspection, and the color-coded embedding media and microscope slides used therewith.

2. Description of the Invention Background

The tracking of multiple samples of biological tissue while preparing that tissue for microscopic evaluation has always presented a problem to laboratory personnel. Multiple samples of tissue may be obtained for microscopic evaluation from, for example, human patients or animals during biopsy, surgery, or autopsy. Typically, during preparation for such evaluation, these tissue samples are first placed in a refrigerated chamber and frozen in a matrix of an embedding medium composed of aqueous resins; the frozen sample/medium is then cut into thin sections on a microtome within the refrigerated chamber; the individual sections are positioned on glass microscope slides; the samples are further processed, usually by staining with one or a series of chemical solutions; and a glass coverslip is placed over the stained samples. This general preparation technique, including the use of a matrix of frozen aqueous embedding medium to encase the tissue sample, has been in use for at least the past thirty years.

Because of the numerous steps involved in preparing the samples, it is somewhat difficult to track the sources of multiple tissue samples. Tissue samples from the same organ of different patients are typically indistinguishable one from another. The materials used in the embedding and sectioning steps, and the cold temperatures involved, preclude labeling by writing on the samples themselves. When samples from more than one patient must be prepared and sectioned in a narrow time frame, or when one specimen must be divided into several parts for independent examination of each part, it is often difficult to distinguish between samples and mix-ups may occur while preparing the samples.

Other processes for preparing tissue samples for microscopic inspection are also known. In one such method, the tissue sample is embedded in a paraffin compound before sectioning. The paraffin-embedding procedure requires significantly more time and is more complex than the frozen embedding medium procedure and requires a certain time period wherein the tissue sample must be immersed in a fixative solution. Consequently, the quicker frozen embedding medium procedure is commonly employed when evaluation of the tissue sample is needed immediately, for example, while a surgical procedure is being performed. Because the tissue samples may be prepared quickly when using the frozen embedding medium procedure, the possibility that samples will be misidentified is magnified. Because the results of the microscopic inspection of the tissue may, for example, affect the course of ongoing surgery, the consequences of misidentification may be grave.

One method of tissue sample identification is often used during the above-mentioned paraffin-embedding procedure. In that procedure plastic tissue cassettes may be used to enclose the sample during and after processing. The tissue cassettes typically are composed of a material which allows labeling with, for example, a permanent marker. However, in preparing tissue samples which are embedded in a matrix of frozen embedding medium, the cold temperatures involved do not allow labeling of any specimen holders which may be used.

Although a need for some means of identifying tissue samples processed using a matrix of frozen aqueous embedding media has existed for at least the past thirty years, the problem remains. Accordingly, it is desirable to provide a method for quickly and easily identifying and tracking samples of biological material during the preparation of sections of that material for microscopic inspection. The method must allow identification of the material from the initial step of freezing the material in embedding medium to the final step of mounting and staining the material on microscope slides.

SUMMARY OF THE INVENTION

To address the problems set forth above, the invention provides a system for identifying and tracking samples of biological material during the preparation of that material for microscopic inspection wherein the above-described frozen embedding media procedure is used. The system includes the use of two or more colored embedding media, the colors being easily distinguishable to the naked eye in both their liquid and frozen states. The identification system may also include microscope slides which are marked with indicia such as, for example, words, symbols, or colors, corresponding to the colors of the various embedding media. In addition, the identification system may include for each of the various colored embedding media a separate container marked with indicia identifying the color of embedding medium stored in the container.

The present invention also discloses a process for preparing biological material for microscopic inspection in which the above-listed colored embedding media, correspondingly marked microscope slides, and, optionally, correspondingly marked embedding media containers may be used.

Finally, the present invention provides for compositions of colored embedding media which include one or more coloring agents. Preferably, those coloring agents are commonly available food coloring compounds such as, for example, FD&C food colorings including FD&C Blue #1, FD&C Red #3, FD&C Yellow #5 or mixtures of those compounds.

By using the colored embedding media alone or in conjunction with the other elements herein-described, the identities of samples of biological material may be quickly and easily tracked during preparation for inspection and evaluation under a microscope. It is believed that these and other advantages will be apparent to those skilled in the art from the following detailed description of the invention.

DETAILED DESCRIPTION OF THE INVENTION

In general, the process for producing sectioned frozen tissue samples for microscopic inspection includes a number of steps, several of which are performed in a refrigerated chamber known generically as a cryostat. One example is Model No. 620 distributed by Anglia Scientific Instruments, Ltd., headquartered in Cottenham, Cambridge, England. That model includes a refrigerated work space of approximately 1½ square feet. Although the preparation process may be performed at varying temperatures within the cryostat, the temperature should be no greater than about −15° C. More commonly, the process steps performed within the work space are carried out at temperatures of −20° to −30° C.

Within the confines of the cryostat's work space are positioned (i) a chuck for producing and holding the frozen embedded tissue sample and (ii) a microtome for sectioning the sample into portions appropriate for inspection under a microscope. The chuck is typically a small metallic object holder with a grooved or perforated surface and is somewhat larger than the size of the desired frozen sample. The chuck is placed into the cryostat a certain amount of time before the frozen sample is produced so that the metal of the chuck is cooled to the temperature of the work space and the embedding media will freeze when it contacts the cold metal.

In a first step of the preparation process, the tissue sample of interest is suspended within a matrix of frozen aqueous embedding medium to produce a frozen embedded sample. Typically, to produce the frozen embedded sample, a portion of the desired embedding medium is introduced onto the chuck. The tissue sample is then placed into the embedding medium on the chuck, and further embedding medium is placed onto the chuck around and on top of the sample. On pressing a heat extractor onto the sample, the embedding medium freezes, encasing the tissue sample within a disk-shaped matrix of frozen embedding medium.

The present invention utilizes a plurality of colored embedding media to differentiate between tissue samples while those samples are in the frozen embedded state. Embedding media used to produce frozen samples typically consist of viscous solutions of water soluble polymers which, when frozen, allow smooth passage of a microtome knife blade. At present, the most widely used embedding medium is sold under the trademark Tissue-Tek by Miles Laboratories, Inc., Elkhart, Ind. The Tissue-Tek medium is also known by the common name "O.C.T. compound" for "optimal cutting temperature". With one exception, embedding media which have been available appear clear and colorless to slightly translucent in the liquid state. On freezing, these embedding media become an opaque white, one frozen medium indistinguishable from another. It is believed that the single exception to the colorless character of the embedding media which have been marketed is a blue-colored embedding medium which was manufactured and sold by Shandon Inc., Pittsburgh, Pa., and which is no longer commercially available. The coloring agent which was used in the Shandon product, methylene blue, is a toxic compound recognized as a biological and bacterial stain. On freezing, the blue Shandon embedding medium becomes opaque, but retains its characteristic blue color.

The present invention contemplates that an array of embedding media having easily distinguishable colors in the liquid state will be used to prepare the frozen embedded samples, the colors being substantially preserved when the media are in the frozen state. A preferred composition for the basic components of the embedding medium of the present invention is shown in Table 1. The percentages of each of the listed components are, as indicated, provided either as weight-per-weight ("w/w") or weight-per-volume ("w/v") percentages of the total aqueous solution weight or volume, respectively.

TABLE 1

| Basic Components of Embedding Media | |
|---|---|
| Polyvinyl alcohol | 10.24% w/w |
| Polyethylene glycol | 4.26% w/w |
| Benzalkonium chloride | 0.25% w/v |

The benzalkonium chloride is added as a preservative. It is to be understood that the composition listed in Table 1 is a preferred composition and that one of ordinary skill in the art could formulate various other compositions, including compositions having other polymers and preservative compounds, which have properties appropriate for use in the sample preparation procedure. In addition, it is believed that the principal components of commercially available embedding media are typically listed on the containers or packaging of those products. As such, the number of possible formulations for embedding media which are within the skill of the art include those which are or have been so-labeled.

With respect to the preferred composition, it is also contemplated that the above-stated proportions may be varied without significantly effecting the properties of that composition and that a variety of other components may be included therein, including various other preservative compounds. Such other components will be known to those of ordinary skill in the art.

The composition of Table 1 will provide a clear, colorless embedding medium which becomes opaque white on freezing. It has been found that certain coloring agents may be added to the basic embedding medium formulation to color the medium in both the liquid and frozen states without adversely affecting the medium's essential properties. The identities of the coloring agents which have been used to produce the colored embedding media of the present invention, the preferred addition amounts of those agents, and the resulting color of the embedding media are provided in Table 2. All preferred additions in Table 2 are given as weight per volume percentages of the total aqueous solution volume.

TABLE 2

| | Embedding Media Coloring Agents | | |
|---|---|---|---|
| Embedding Media Color Achieved | Coloring Agent Chemical Formula | Coloring Agent Common Name | Preferred Addition |
| Blue | $C_{17}H_{34}N_2Na_2O_9S_3$ | FD&C Blue #1 | 0.02% |
| Red | $C_{20}H_6I_4Na_2O_5$ | FD&C Red #3 | 0.025% |
| Yellow | $C_{16}H_9N_4Na_3O_9S_2$ | FD&C Yellow #5 | 0.025% |
| Green | See Above | Mixture of FD&C Yellow #5 and FD&C Blue #1 | 0.0125% yellow and 0.0100% |

TABLE 2-continued

| Embedding Media Coloring Agents | | | |
|---|---|---|---|
| Embedding Media Color Achieved | Coloring Agent Chemical Formula | Coloring Agent Common Name | Preferred Addition |
| | | | blue |

Although the above-disclosed preferred coloring agents are commonly available in solution as familiar household food colorings, it is preferred that the coloring agents be added to the basic composition in Table 1 in their pure powdered forms. It is believed that the actual amount of the coloring agent which may be added to the embedding media can vary widely, by as much as ten fold times greater or less than the above-stated amounts, and still produce an embedding medium with acceptable properties. Such acceptable embedding media must sufficiently color the media so that the color is apparent to the naked eye in both the liquid and frozen states, but without either (i) staining or otherwise coloring the embedded tissue sample or (ii) significantly inhibiting the staining of the tissue sample by the staining solutions. A colored embedding medium would be considered to significantly inhibit the staining of the tissue sample if the embedding medium prevented the staining solution from coloring the sample so as to allow inspection of the sample under a microscope.

It is believed that concentrations of the above-disclosed coloring agents in the range of about 0.001% to about 0.3% on a weight per volume basis may be used to produce an acceptable embedding medium. However, it is preferred that the coloring agents be employed in the range of about 0.01% to about 0.03% on a weight per volume basis. It has also been found that the above coloring agents will stain the tissue samples if used in relatively high concentrations, on the order of approximately 1% weight per volume or more.

Although four examples of embedding media coloring agents have been provided in Table 2, it is believed that other available coloring agents may be employed in like fashion, including those coloring agents recognized either as food colorings, such as the FD&C food colorings, or as biological stains. In addition, it is to be understood that solutions of, for example, the above-disclosed coloring agents, may be combined in various proportions to produce a number of other colors. For example, with respect to the coloring agents listed in Table 2, solutions of FD&C Blue #1 and FD&C Red #3 may be combined in amounts appropriate to produce a purple coloring compound, while solutions of FD&C Yellow #5 and FD&C Red #3 may be combined to produce an orange coloring compound. Determining the proper proportions of those coloring agents necessary to form additional colors could be accomplished by one of skill in the art without undue effort. In addition to combining isolated coloring agent solutions to achieve other coloring agents, colored embedding media which have already been prepared in certain colors could be mixed with colored embedding media of other colors to produce still more colors of embedding media. The additional colors of embedding media could be pre-prepared and stored in individual containers, or could be mixed just prior to use.

In utilizing the above-described colored embedding media, the tissue samples which are to be differentiated one from another are frozen on the chuck in embedding media having the various different colors. Consequently, tissue samples embedded therein may be quickly and easily distinguished by the colors of the frozen embedding media matrices.

In a second step of the process, the frozen embedded tissue sample is then cut or sectioned into portions having a thickness appropriate for microscopic inspection. The desired thickness of the sectioned sample is typically about four microns, but may vary. Typically, after the tissue sample is frozen in the colored embedding medium, the heat extractor is removed and the chuck, bearing frozen embedding medium with the tissue sample frozen within it, is placed on a holder which allows sectioning on the microtome within the cryostat. The microtome typically slices the sample into thin sections by sliding the frozen embedded sample up and down against the blade of the microtome. The microtome produces a sectioned sample consisting of a thinly sliced tissue sample frozen to a thin margin of embedding medium. Because the section is very thin, the color of the frozen embedding medium is typically not distinguishable.

In a third step of the process, after the sample is sectioned, it is immediately placed on a microscope slide, removed from the cryostat, and the embedding media is removed from the sectioned tissue sample. Commonly, microscope slides include a painted or frosted square or rectangular area, usually at one end of the slide. In addition, microscope slides may have their unpainted glass surfaces coated with various agents to increase the adhesion of the tissue sample on the slide. On placing the sectioned frozen sample onto the slide, appropriate words or symbols may be marked directly on the frosted or painted area to identify the sample.

In a preferred embodiment, the colored embedding media may be sold in a kit form which includes microscope slides marked with colors corresponding to the colors of the embedding media used. In that case, the sectioned samples are immediately placed onto a microscope slide having a colored area matching the color of the embedding medium in which the tissue sample was frozen. For the convenience of color-blind users, the microscope slides may include a universally recognized symbol corresponding to the colors of the embedding media used, the printed word for that color, or both. The symbol or wording may be used on the microscope slide either alone or in combination with the actual color. Other possibilities include a kit including a plurality of colored embedding media, quickly recognizable containers for the media, and correspondingly labeled microscope slides, the latter two of which could be labeled with an actual color, a symbol for that color, or both. Additional possibilities would be obvious to those of skill in the art, all of which are intended to be encompassed by the present invention. In the case of any of the above-described embodiments, the possibility of confusion between tissue samples during preparation for microscopic inspection is greatly reduced.

So that the embedding media do not obscure the colors produced in the tissue sample on treating the tissue with staining compounds, the embedding media must be removed from the microscope slide before viewing under the microscope. The embedding medium is first returned to the liquid state by warming the slide to room temperature. The embedding media may then be removed by, for example, dissolving the media in either water or alcohol. However, other techniques for removing the embedding media will be apparent to those of skill in the art. Typically, the embedding media is dissolved by applying ethyl alcohol to the sectioned tissue sample on the microscope slide. In addition to removing the embedding media, the ethyl alcohol acts to pretreat the sample to be stained because it fixes the tissue elements in their natural states. In the alternative, the sample may be directly immersed in the staining solution, whereby the staining solution stains the tissue sample and the solvent of the staining solution dissolves and rinses away the embedding media.

In the fourth and final step of the process, the tissue sample on the microscope slide is treated with staining compounds. The most commonly used biological tissue staining compounds are hematoxylin and eosin. In experimental trials, both of these staining compounds have been used to stain tissue samples which were embedded in matrices of each of the four colored embedding media, each individual embedding medium having the general composition shown in Tables 1 and one of the coloring agents listed in Table 2. The frozen embedded samples were then sectioned as described above. It was found that those embedding media neither stained the tissue samples nor significantly inhibited the hematoxylin or eosin staining solutions from staining the tissue samples. It is believed that other staining compounds may be used to stain tissue which has been embedded in the colored embedding media of the present invention without those embedding media significantly inhibiting the staining of the tissue samples. It is to be understood that it is within the skill of the art to determine the compatibility of other staining compounds with tissue samples embedded in and sectioned using the colored embedding media of the present invention.

The foregoing detailed description is provided to explain the invention and its advantages. It is to be appreciated, however, that variations and changes could be made to the invention described above without departing from the spirit and scope of the invention as claimed.

What is claimed is:

1. A kit for identifying and tracking biological material during preparation for microscopic inspection, the kit comprising a plurality of colored aqueous embedding media, each of said media having a color which is different, and distinguishable to the naked eye, from the color of each other said media and which is substantially retained when said media are frozen, said media being used to embed samples of the biological material for freezing and sectioning, said media neither staining nor otherwise coloring said biological material, so that following sectioning, different samples of said sectioned, embedded biological material are identifiable by said different colors.

2. The kit recited in claim 1 wherein said colored embedding media do not significantly inhibit the staining of said biological material by staining compounds.

3. The kit recited in claim 2 wherein said staining compounds are selected form the group consisting of hematoxylin and eosin.

4. The kit recited in claim 2 further comprising microscope slides, each of said slides having a portion thereof marked with indicia corresponding to a color of one of said colored embedding media, said microscope slides being used to mount said sectioned, embedded biological material for inspection under a microscope.

5. The kit recited in claim 4 wherein said indicia are colors corresponding to the colors of said colored embedding media.

6. The kit recited in claim 4 wherein said indicia are words or other symbols corresponding to the colors of said colored embedding media.

7. The kit recited in claim 4 further comprising individual containers for said colored embedding media, each of said containers having an area marked with indicia corresponding to the color of embedding media stored therein.

8. A process for preparing biological material for microscopic inspection, the process comprising the steps of:
    embedding at least a portion of the biological material in a matrix of a frozen aqueous embedding medium, said embedding medium having a characteristic color in the liquid state, which color is substantially preserved when said embedding medium is frozen, said embedding medium neither staining nor otherwise coloring said embedded biological material;
    cutting the embedded biological material into at least one frozen section having a thickness appropriate for microscopic inspection, said section comprising at least a portion of said biological material and a margin of frozen colored embedding medium;
    positioning said frozen section on a microscope slide, said slide marked to identify the color of the embedding medium attached to said frozen section; and
    staining said section of biological material with a staining compound.

9. The process recited in claim 8 wherein said microscope slide comprises portions having a color corresponding to the color of said colored embedding media attached to said section on said microscope slide.

10. The process of claim 8 wherein said microscope slide comprises portions having words or other symbols corresponding to the color of said colored embedding media attached to said section on said microscope slide.

11. The process of claim 8 wherein the embedding step further comprises dispensing the colored embedding medium from a container having indicia corresponding to the color of the embedding medium contained therein.

12. The process of claim 8 wherein said embedding medium comprises polyvinyl alcohol, polyethylene glycol, a preservative compound, and one or more coloring agents which are effective to color the medium in both the liquid and frozen states.

13. The process of claim 12 wherein said preservative compound is benzalkonium chloride.

14. The process of claim 13 wherein said embedding medium comprises:
    about 10.24% polyvinyl alcohol on a weight per weight basis;
    about 4.26% polyethylene glycol on a weight per weight basis;
    about 0.25% benzalkonium chloride on a weight per volume basis; and
    about 0.01% to about 0.03% of one or a mixture of coloring agents on a weight per volume basis.

15. The process recited in any of claims 12 through 14, wherein said coloring agents are food colorings.

16. The process of claim 15 wherein said food colorings are one or more FD&C dyes.

17. The process recited in claim 16 wherein said FD&C dyes are one or more selected from the group consisting of FD&C Blue #1, FD&C Red #3, and FD&C Yellow #5.

18. A colored aqueous solution consisting essentially of polyvinyl alcohol, polyethylene glycol, a preservative compound, and a coloring agent which is effective to color the solution when the solution is in either a liquid or frozen state, said solution being used for embedding a sample of biological material in a frozen matrix of the solution so that the sample may be sectioned for microscopic inspection.

19. The colored aqueous solution of claim 18 wherein said preservative compound is benzalkonium chloride.

20. The colored aqueous solution of claim 19, comprising:

about 10.24% polyvinyl alcohol on a weight per weight basis;

about 4.26% polyethylene glycol on a weight per weight basis;

about 0.25% benzalkonium chloride on a weight per volume basis; and a coloring agent which is effective to color the solution in either a liquid or frozen state.

21. The colored aqueous solution of claim 20 wherein said coloring agent is present in a range of about 0.001% to about 0.03% on a weight per volume basis.

22. The colored aqueous solution of claim 21 wherein said coloring agent is present in a range of about 0.01% to about 0.03% on a weight per volume basis.

23. The colored aqueous solution of any of claims 20 through 22 wherein said coloring agent comprises one or more food colorings.

24. The colored aqueous solution of claim 23 wherein said food colorings are one or more FD&C dyes.

25. The colored aqueous solution of claim 24 wherein said FD&C dyes are FD&C Blue #1, FD&C Red #3, and FD&C Yellow #5, and combinations thereof.

* * * * *

UNITED STATES PATENT AND TRADEMARK OFFICE
CERTIFICATE OF CORRECTION

PATENT NO. : 5,416,029
DATED : May 16, 1995
INVENTOR(S) : Beverly W. Miller, William J. Hayes It is certified that error appears in the above-indentified patent and that said Letters Patent is hereby corrected as shown below:

Column 4:

Table 2, line 5, delete [$C_{17}H_{34}N_2Na_2O_9S_3$] and substitute with -- $C_{37}H_{34}N_2Na_2O_9S_3$ --.

Column 5, line 29, delete [0,001%] and substitute with -- 0.001% --.

Signed and Sealed this

Twelfth Day of September, 1995

Attest:

BRUCE LEHMAN

*Attesting Officer*  *Commissioner of Patents and Trademarks*